(12) United States Patent
Ferro Flores et al.

(10) Patent No.: US 12,128,114 B2
(45) Date of Patent: Oct. 29, 2024

(54) $^{177}$Lu-DOTA-HYNIC-IPSMA AS A THERAPEUTIC RADIOPHARMACEUTICAL TARGETING PROSTATE-SPECIFIC MEMBRANE ANTIGEN

(71) Applicant: INSTITUTO NACIONAL DE INVESTIGACIONES NUCLEARES, Estado de México (MX)

(72) Inventors: Guillermina Ferro Flores, Estado de México (MX); Blanca Elí Ocampo García, Estado de México (MX); Myrna Alejandra Luna Gutiérrez, Estado de México (MX); Clara Leticia Santos Cuevas, Estado de México (MX); Erika Patricia Azorín Vega, Estado de México (MX); Nallely Patricia Jiménez Mancilla, Estado de México (MX); Tania Hernández Jiménez, Estado de México (MX); Flor de María Ramírez De La Cruz, Estado de México (MX)

(73) Assignee: INSTITUTO NACIONAL DE INVESTIGACIONES NUCLEARES, Estado de Mexico (MX)

( * ) Notice: Subject to any disclaimer, the term of this patent is extended or adjusted under 35 U.S.C. 154(b) by 728 days.

(21) Appl. No.: 16/980,252

(22) PCT Filed: Mar. 7, 2019

(86) PCT No.: PCT/MX2019/000025
§ 371 (c)(1),
(2) Date: Sep. 11, 2020

(87) PCT Pub. No.: WO2019/177449
PCT Pub. Date: Sep. 19, 2019

(65) Prior Publication Data
US 2021/0015949 A1    Jan. 21, 2021

(30) Foreign Application Priority Data
Mar. 14, 2018    (MX) .................... MX/a/2018/003175

(51) Int. Cl.
*A61K 51/00*    (2006.01)
*A61K 51/04*    (2006.01)
*A61M 36/14*    (2006.01)

(52) U.S. Cl.
CPC .................. *A61K 51/041* (2013.01)

(58) Field of Classification Search
CPC .............. A61K 51/041; A61K 51/0402; A61K 51/0497; C07F 5/003; A61P 35/00; C07D 401/12

See application file for complete search history.

(56) References Cited

U.S. PATENT DOCUMENTS

2016/0228587 A1    8/2016 Eder et al.
2017/0296684 A1    10/2017 Driver et al.
(Continued)

FOREIGN PATENT DOCUMENTS

MX            336322 B       1/2016
WO       2007005491 A1       1/2007
(Continued)

OTHER PUBLICATIONS

Santos-Cuevas et al. (Nucl. Med. Biol. 2017, 52, 1-6).*
(Continued)

*Primary Examiner* — Michael G. Hartley
*Assistant Examiner* — Melissa J Perreira
(74) *Attorney, Agent, or Firm* — Amster, Rothstein & Ebenstein LLP

(57) ABSTRACT

The invention relates to a new lutetium-177 therapeutic radiopharmaceutical as an inhibitor of prostate-specific membrane antigen (iPSMA), wherein 1,4,7,10-tetraazacyclododecane-N,N',N'',N''''-tetraacetic acid (DOTA) bonded to the heterocyclic molecule hydrazinonicotinamide (HYNIC), generates a rigid chemical structure that minimises the number of conformers and intramolecular hydrogen bonds, thereby producing a favourable spatial orientation of the active site (Lys(Nal)-NH—CO—NH-Glu) in the molecule, for biological recognition by the PSMA protein. The new 177Lu-DOTA-HYNIC-iPSMA radiopharmaceutical accumulates, with high affinity in vivo, in tumours that overexpress the PSMA protein, acting as a radiotherapeutic agent. The purpose of the invention is to provide a new specific radiopharmaceutical (molecular target radiopharmaceutical) for the treatment of tumours with PSMA overexpression.

(Continued)

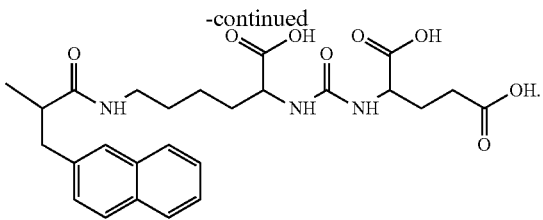

10 Claims, 6 Drawing Sheets

(56) References Cited

U.S. PATENT DOCUMENTS

| | | | |
|---|---|---|---|
| 2019/0008988 | A1 | 1/2019 | Eder et al. |
| 2019/0060491 | A1 | 2/2019 | Eder et al. |
| 2019/0336622 | A1 | 11/2019 | Eder et al. |
| 2019/0343970 | A1 | 11/2019 | Ferro Flores et al. |
| 2019/0374660 | A1 | 12/2019 | Eder et al. |
| 2020/0138985 | A1 | 5/2020 | Shalom |
| 2021/0177996 | A1 | 6/2021 | Eder et al. |
| 2021/0187132 | A1 | 6/2021 | Ferro Flores et al. |
| 2021/0283279 | A1 | 9/2021 | Eder et al. |

FOREIGN PATENT DOCUMENTS

| | | |
|---|---|---|
| WO | 2015055318 A1 | 4/2015 |
| WO | 2016046793 A2 | 3/2016 |
| WO | 2017222362 A1 | 12/2017 |
| WO | WO-2022178592 A1 * | 9/2022 |

OTHER PUBLICATIONS

Rendon, J.R. (2017) "Development of a multidose lyophilized formulation for the preparation of 177Lu-DOTA-iPSMA" [Biotechnology Engineer Thesis] Tran Polytechnic University of the Valley of Toluca.*
Gutierrez et al. (J. Radioanal. Nucl. Chem. 2017, 314, 2181-2188).*
Plichta et al. (int. J. Mol. Sci. 2021, 22, 12095).*
Ferro-Flores et al. (Nucl. Med. Biol. 2017, 48, 36-44).*
Maresca et al. (J. Med. Chem. 2009, 52, 347-357).*
Luna-Gutierrez et al. (Pharmaceutics 2023, 15, 1988).*
Hernandez-Jimenez et al. (J. Radioanal. Nucl. Chem. 2018, 318, 2059-2066).*
Santos-Cuevas et al. (Contrast Media Mol. Imaging 2018, 2018, 5247153).*
Kratochwil et al. (J. Nucl. Med. 2017, 48, 36-44).*
Kratochwil et al. 2016, 57(8), 1170-1176.*
International Search Report and Written Opinion dated Jun. 21, 2019 from PCT International Appln. No. PCT/MX2019/000025 (in Spanish with English language translation of International Search Report attached).

Xu et al., "99mTc-Labeling and Evaluation of a HYNIC Modified Small-Molecular Inhibitor of Prostate-Specific Membrane Antigen," Nuclear Medicine and Biology, vol. 48, 2017, pp. 69-75.
Ferro Flores et al., "Clinical Translation of a PSMA Inhibitor for 99mTc-Based SPECT," Nuclear Medicine and Biology, vol. 48, 2017, pp. 36-44.
Hillier et al., "99mTc-Labeled Small-Molecule Inhibitors or Prostate-Specific Membrane Antigen for Molecular Imaging of Prostate Cancer," J. Nucl. Med., vol. 54, Jun. 3, 2013, pp. 1369-1376.
Instituto Mexicano de la Propiedad Industrial (IMPI), "Examination Report," issued in Mexican Patent Application No. MX/a/2018/003175, which is a counterpart to U.S. Appl. No. 16/980,252, mailed on Jul. 13, 2020, 5 pages.
Mónica Janet Mendoza Figueroa, "Tesis: Marcado, estabilidad y evaluación in vitro de inhibidores carboxipeptidasa II," Ciudad Universitaria, Ciudad de México: UNAM, 2016.
Richard P. Baum et al., "177Lu-Labeled Prostate-Specific Membrane Antigen Radioligand Therapy of Metastatic Castration-Resistant Prostate Cancer: Safety and Efficacy," The Journal of Nuclear Medicine, vol. 57, No. 7, pp. 1006-1103, Jul. 2016, doi: 10.2967/jnumed.115.168443.
Communication Supplementary European Search Report dated Jan. 10, 2022 in connection with European Patent Application No. 19768668.6.
Clara Santos-Cuevas et al: "177 Lu-DOTA-HYNIC-Lys(Nal)-Urea-Glu: Biokinetics, Dosimetry, and Evaluation in Patients with Advanced Prostate Cancer", Contrast Media & Molecular Imaging, vol. 2018, Nov. 11, 2018 (Nov. 11, 2018), pp. 1-10, XP055685809.
Tania Hernandez-Jimenez: "77 Lu-DOTA-HYNIC-Lys(Nal)-Urea-Glu: synthesis and assessment of the ability to target the prostate specific membrane antigen Nallely Jime nez-Mancilla 3 @BULLET", Journal of Radioanalytical and Nuclear Chemistry, Oct. 9, 2018 (Oct. 9, 2018), pp. 2059-2066, XP055876938, DOI: 10.1007/s10967-018-6239-9 Retrieved from the Internet:URL: https://link.springer.com/content/pdf/10.1007/s10967-018-6239-9.pdf.
Guillermina Ferro-Flores et al: "Clinical translation of a PSMA inhibitor for99mTc-based SPECT", Nucl. Med. Biol, Elsevier, NY, US, vol. 48, Feb. 3, 2017 (Feb. 3, 2017), pp. 36-44, XP029963241.
M. Benesova et al: "Preclinical Evaluation of a Tailor-Made DOTA-Conjugated PSMA Inhibitor with Optimized Linker Moiety for Imaging and Endoradiotherapy of Prostate Cancer", The Journal of Nuclear Medicine, vol. 56, No. 6, Apr. 16, 2015 (Apr. 16, 2015), pp. 914-920, XP055289291.
Thomas D. Harris: "Preparation of amino acid and peptide hydrazide conjugates as imaging agents", (W02007005491 AI), Jan. 1, 2007 (Jan. 1, 2007), pp. 1-3, XP055876939.
Intellectual Property India, "Office Action," issued in Indian Patent Application No. 202017042400, which is a counterpart to U.S. Appl. No. 16/980,252, mailed on Mar. 31, 2022, 6 pages.
Kambiz Rahbar et al., "Response and Tolerability of a Single Dose of 177Lu-PSMA-617 in Patients with Metastatic Castration-Resistant Prostate Cancer: A Multicenter Retrospective Analysis," The Journal of Nuclear Medicine, vol. 57, No. 9, Sep. 2016, pp. 1334-1338, DOI: https://doi.org/10.2967/jnumed.116.173757.

* cited by examiner

$^{177}$Lu-DOTA-HYNIC-IPSMA AS A THERAPEUTIC RADIOPHARMACEUTICAL TARGETING PROSTATE-SPECIFIC MEMBRANE ANTIGEN

CROSS-REFERENCE TO RELATED APPLICATIONS

This application is a U.S. national stage entry under 35 U.S.C. § 371 of PCT International Patent Application No. PCT/MX2019/000025, filed Mar. 7, 2019, which claims priority to Mexican Patent Application No. MX/a/2018/003175, filed Mar. 14, 2018, the contents of each of which are incorporated herein by reference in their entirety.

DESCRIPTION

Technical Field of the Invention

The present invention relates to a novel lutetium-177 therapeutic radiopharmaceutical as a prostate-specific membrane antigen inhibitor (iPSMA) wherein 1,4,7,10-tetraazacyclododecano-N,N',N'',N'''-tetraacetic acid (DOTA) bound to the molecule hydrazinonicotinamide (HYNIC), which is heterocyclic in nature, generates a rigid chemical structure that minimises the number of conformers and intramolecular hydrogen bonds, thereby resulting in a spatial orientation of the active site (Lys(Nal)-NH—CO—NH-Glu) in the molecule that favors biological recognition of the PSMA protein. The novel radiopharmaceutical $^{177}$Lu-DOTA-HYNIC-iPSMA accumulates in tumors overexpressing the protein PSMA with high affinity in vivo, thereby acting as a radiotherapeutic agent.

Background

Prostate cancer (PC) is the second most common cancer amongst males worldwide [Jemal A, et al. *Cancer statistics, 2010. CA Cancer J Clin.* 2010, 60: 277-300]. In patients with localised PC, the five-year survival rate is close to 100%, whereas in patients with metastasis, the five-year survival rate is 31% [Wei 0, et al. *Global analysis of differentially expressed genes in androgen-independent prostate cancer. Prostate Cancer Prostatic Dis.* 2007, 10: 167-174]. Almost all patients with metastasis respond well to anti-androgen treatments initially. However, the main cause of death in PC patients is progression to androgen independence.

The enzyme glutamate carboxypeptidase II, also known as prostate-specific membrane antigen (PSMA) is expressed in epithelial cells in the prostate and is highly overexpressed in 95% of advanced prostate cancers. PSMA expression levels are directly correlated with the androgen independence, metastasis and progression of PC [Santoni M., et al. *Targeting prostate-specific membrane antigen for personalized therapies in prostate cancer: morphologic and molecular backgrounds and future promises. J Biol Regul Homeost Agents.* 2014, 28: 555-563] As such, PSMA is an appropriate molecular target for the image-based detection and radiotherapy of metastatic prostate cancer using specific radiopharmaceuticals.

The PSMA gene comprises 19 exons representing approximately 60 kb of genomic DNA. This gene codes for a type II transmembrane protein with a short cytoplasmic fragment (19 amino acids), a hydrophobic transmembrane domain (24 amino acids), and a large extracellular domain (707 amino acids). PSMA contains Zn at the active center of the enzyme, therefore the sequence Glu-NH—CO—NH-Lys (β-naphthyl alanine)=Glu-NH—CO—NH-Lys(Nal) has been proposed as an effective inhibitor of the activity thereof [Benesová, M, et al., *Preclinical evaluation of a tailor-made DOTA-conjugated PSMA inhibitor with optimized linker moiety for imaging and endoradiotherapy of prostate cancer. J Nucl Med,* 56, 2015: 914-920]. In the specific chemical interaction, the three carboxyl groups of the Glu-NH—CO—NH-Lys fragment interact electrostatically with the peptide side-chains at the active site of PSMA, the urea oxygen coordinates to zinc, and the aromatic structure in Nal interacts to ensure coupling with the active hydrophobic site in the enzyme. Recent clinical studies have shown that the application of two different PSMA inhibitor derivatives labeled with Lu-177, namely $^{177}$Lu-PSMA-617 and $^{177}$Lu-PSMA-I&T, results in a significant reduction in prostate antigen (PSA) levels in 50-70% of PC patients, with no severe side-effects, thereby significantly increasing patient survival [Ahmadzadehfar H., et al. *Early side effects and first results of radioligand therapy with $^{177}$Lu-DKFZ-617 PSMA of castrate-resistant metastatic prostate cancer: a two-centre study. EJNNMMI Res.* 2015. 5:36; Kratochwil C et al. [$^{177}$Lu]*Lutetium-labelled PSMA ligand-induced remission in a patient with metastatic prostate cancer. Eur J Nucl Med Mol Imaging,* 42, 2015: 987-988; Weineisen M. et al., $^{68}$*Ga- and $^{177}$Lu-Labeled PSMA I&T: Optimization of a PSMA-Targeted Theranostic Concept and First Proof-of-Concept Human Studies. J Nucl Med* 2015; 56:1169-1176; Baum, R. P., et al. *Lutetium-177 PSMA radioligand therapy of metastatic castration-resistant prostate cancer: safety and efficacy. J Nucl Med,* 2016, 57:1006-1013; Kratochwil, C, et al. *PSMA-targeted radionuclide therapy of metastatic castration-resistant prostate cancer with Lu-177 labeled PSMA-617. J Nucl Med,* 2016, 57:1170-1176; Rahbar, K et al. *Response to and tolerability of a single dose of $^{177}$Lu-PSMA-617 in patients with metastatic castration-resistant prostate cancer: a multicenter retrospective analysis. J Nucl Med,* 2016, 57:1334-1338; Rahbar, K et al. *German Multicenter Study Investigating $^{177}$Lu-PSMA-617 Radioligand Therapy in Advanced Prostate Cancer Patients. J Nucl Med,* 2017, 58:85-90]. The PSMA protein is multifunctional as it can act as an internalization receptor, a nutrient absorption enzyme, or as a peptidase that plays a role in signal transduction in epithelial cells and in cell migration [Rajasekaran A. et al. *Is prostate-specific membrane antigen a multifunctional protein? American Journal of Physiology—Cell Physiology.* 2005, 288:C975-C981]. As such, PSMA-inhibiting radiopharmaceuticals may also be used in neoplasms other than PC, for example in metastatic breast cancer, osteosarcoma, glioma and differentiated thyroid cancer, amongst others [la Fougére, et al. *In vivo visualization of prostate-specific membrane antigen in glioblastoma. Eur J Nucl Med and Mol Imaging,* 2015, 42: 170-171; Verburg F A, et al. *First evidence of PSMA expression in differentiated thyroid cancer using [$^{68}$Ga] PSMA-HBED-CC PET/CT Eur J Nucl Med and Mol imaging,* 2015, 42: 1622-1623; Zeng C et al. *Prostate-specific membrane antigen: a new potential prognostic marker of osteosarcoma. Medical Oncology,* 2012, 29: 2234-2239; Sathekge M el al, $^{68}$*Ga-PSMA imaging of metastatic breast cancer. Eur J Nucl Med and Mol Imaging,* 2015, 42:1482-1483].

However, prior to any radiotherapy treatment, uptake of the radiopharmaceutical in tumors or their metastases must be evaluated by nuclear imaging in order to confirm whether treatment will be useful for the patient or not and to determine the activity that will need to be administered to provide the ablative dose of radiation to the tumors, in other words personalised and theranostic medicine is applied. To that end, diagnostic PSMA-inhibiting radiopharmaceuticals must be used to obtain molecular images by positron-emission tomography (PET) or single-photon emission computed tomography (SPECT), with $^{68}$Ga-PSMA-11 (PET) being the most widely used in clinical practice in this regard due to its high sensitivity and specificity [Eder M et al. *Novel preclinical and radiopharmaceutical aspects of [68Ga]Ga-PSMA-HBED-CC: a new PET tracer for imaging of prostate cancer. Pharmaceuticals*, 2014, 7: 779-796; Eder M et al. *68Ga-complex lipophilicity and the targeting property of a urea-based PSMA inhibitor for PET imaging. Bioconjugate Chem*, 2012, 23:688-697; Weineisen et al. *68Ga- and 177Lu-labeled PSMA I&T: optimization of a PSMA-targeted theranostic concept and first proof-of-concept human studies." J Nucl Med*, 2015, 56: 1169-1176; Afshar-Oromieh, A., et al. *Comparison of PET/CT and PET/MRI hybrid systems using 68Ga-labeled PSMA ligand for the diagnosis of recurrent prostate cancer: initial experience. Eur J Nucl Med and Molecular Imaging* 41.5 (2014); 887-89 7].

However, both nationally and internationally, SPECT studies represent more than 70% of all studies carried out in nuclear medicine given their lower cost and the greater availability of equipment and radionuclides as there is no need for a cyclotron in hospitals or close to them. The most widely used radionuclide for SPECT imaging is $^{99m}$Tc and, recently, $^{99m}$Tc EDDA/HYNIC-iPSMA was reported as a radiopharmaceutical inhibitor of prostate-specific membrane antigen (iPSMA) containing hydrazinonicotinamide (HYNIC) as a critical chemical group for enhancing the lipophilicity of the molecule for coupling to the hydrophobic sites in PSMA, combined with the conventional use of HYNIC as a chelating agent for the radiometal $^{99m}$Tc, with ethylenediaminoacetic acid (EDDA) being used to complete the coordination sphere of the radiometal. The radiopharmaceutical $^{99m}$Tc-EDDA/HYNIC/iPSMA detects the PSMA protein overexpressed in prostate cancer cells with high in vivo affinity using SPECT molecular imaging techniques in nuclear medicine [Ferro-Flores G., et al. *Clinical translation of a PSMA inhibitor for $^{99m}$Tc-based SPECT. Nucl Med Bici*, 2017, 48:36-44; Santos-Cuevas et al, *$^{99m}$Tc-EDDA/HYNIC-iPSMA: Biokinetics and Radiation Dosimetry in Healthy Subjects and Tumor Imaging in Patients with Prostate Cancer. Nucl Med Biol*, 2017, 52:1-6; Lawal I. O., et al. *Diagnostic sensitivity of Tc-99m HYNIC PSMA SPECT/CT in prostate carcinoma: A comparative analysis with Ga-68 PSMA PET/CT, The Prostate*, 2017, 1-8; Ferro-Flores G., et al. *$^{99m}$Tc-EDDA/HYNIC-iPSMA as a radiopharmaceutical for detecting the overexpression of prostate-specific membrane antigen*, WO2017222362, PCT/MX2017/000068].

In order to develop a theranostic pair for the ligand HYNIC-iPSMA that can be labeled with Lu-177, herein we propose to bind the molecule DOTA to HYNIC, thus generating a rigid chemical structure that minimises the number of conformers and intramolecular hydrogen bonds, thereby resulting in a spatial orientation of the active site (Lys(Nal)-NH—CO—NH-Glu) in the molecule that favors biological recognition of the PSMA protein.

DETAILED DESCRIPTION OF THE INVENTION

Figure 1:
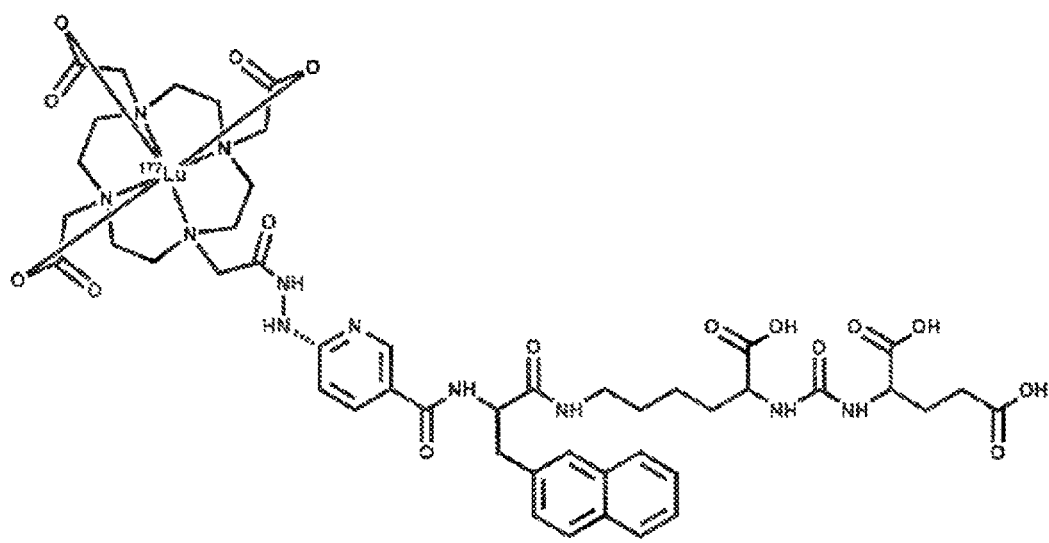
FIG. 1 shows the structure of the radiopharmaceutical 177Lu-DOTA-HYNIC-iPSMA.

A novel lutetium-177 radiopharmaceutical that can inhibit prostate-specific membrane antigen (iPSMA) and which contains 1,4,7,10-tetraazacyclododecano-N,N',N",N"'-tetraacetic acid (DOTA) bound to the hydrazinonicotinamide (HYNIC) molecule, which is heterocyclic in nature, thus generating a rigid chemical structure that minimises the number of conformers and intramolecular hydrogen bonds, thereby resulting in a spatial orientation of the active site (Lys (Nal)-NH—CO—NH-Glu) in the molecule that favors biological recognition of the PSMA protein is presented for patent purposes. The novel radiopharmaceutical $^{177}$Lu-DOTA-HYNIC-iPSMA accumulates in tumors overexpressing the protein PSMA with high affinity in vivo, thereby acting as a radiotherapeutic agent. The structure of the radiopharmaceutical to be patented ($^{177}$Lu-DOTA-HYNIC-iPSMA) is shown in FIG. 1.

Given the common knowledge that, given the heterocyclic nature thereof, pyridine has a dipolar moment and lower resonance energy than that of benzene (117 kJ·mol$^{-1}$ for pyridine versus 150 kJ·mol$^{-1}$ for benzene), as well as a shorter C—N bond (137 pm) compared with the value of 139 pm for the C—C bond in benzene and cyclohexane [Elschenbroich C. *Organometallchemie, 6th ed.*, 2008, ISBN 3-8351-0167-6], the derivative $^{177}$Lu-DOTA-HYNIC-iPSMA was designed and synthesized to obtain a poorly reactive and rigid chemical structure in the HYNIC region that minimises the number of conformers and intramolecular hydrogen bonds with respect to the derivatives $^{177}$Lu-PSMA-617 and $^{177}$Lu-PSMA-I&T. Table 1 below presents the comparative results for the molecular properties and optimal structural geometries of the different PSMA inhibitors. The ligands PSMA-617, DOTA-HYNIC-iPSMA, and PSMA-I&T were constructed taking into account the valence, bonding type, charge, and hybridisation. The minimum energies (obtained using augmented MM3) and lowest energy conformer (CONFLEX procedure) associated with the optimal geometry of the structures thereof were obtained using the CAChe Work System Pro software suite. The optimal geometrical structures were confirmed using quantum mechanical methods with the Schrödinger equation with MOPAC (molecular orbital), which calculates the heat of formation in water (COSMO). The lutetium complexes were constructed from said structures and the augmented MM3 (molecular mechanics) results, CONFLEX, and most stable and optimal geometric structure are presented for the radiopharmaceuticals Lu-PSMA-617 and Lu DOTA-HYNIC-iPSMA and Lu-PSMA-I&T. It can be seen from table 1 that the Lu DOTA-HYNIC-iPSMA molecule is more stable than Lu-PSMA-617 according to the energy of the most stable conformer (lower energy) and the lower total number of conformers, and Lu-DOTA-HYNIC-iPSMA forms fewer hydrogen bonds than Lu-PSMA-617 and Lu-PSMA-I&T. It should be noted that hydrogen bonds play a key role in spatial conformation as, although Lu-PSMA-I&T presents

TABLE 1

MOLECULAR PROPERTIES OF THREE PSMA PROTEIN INHIBITING LIGANDS WITH TUMOR UPTAKE AND RADIOTHERAPEUTIC EFFECT DEMONSTRATED IN CLINICAL STUDIES WHEN COORDINATED TO Lu-177

| CALCULATION (kcal/mol) | PSMA-617 | Lu-PSMA-617 | DOTA-HYNIC-IPSMA | Lu-DOTA-HYNIC-IPSMA | PSMA-I&T | Lu-PSMA-I&T |
|---|---|---|---|---|---|---|
| Minimum energy (MM3) | 87.795 | −49.038 | 106.412 | −76.360 | 105.652 | −81.031 |
| Electrostatic charge | −20.447 | −197.887 | −10.061 | −206.795 | −22.131 | −210.822 |
| Hydrogen bond | 25.317 | 27.070 | 22.253 | 19.984 | 27.304 | 35.499 |
| van der Waals | 45.671 | 58.033 | 50.036 | 71.704 | 50.840 | 127.435 |
| Strength (stretch) | 6.994 | 10.184 | 7.398 | 26.970 | 9.471 | 50.100 |
| Angle | 16.360 | 36.203 | 20.704 | 84.579 | 20.504 | 143.558 |
| Bending strength | 0.937 | 1.196 | 1.117 | 4.282 | 1.180 | 8.849 |
| Dihedral | 14.232 | 32.247 | 15.863 | 42.282 | 20.508 | 83.716 |
| Improper torsion | 0.173 | 0.375 | 0.264 | 0.290 | 0.207 | 1.064 |
| Torsion strength | −1.288 | −1.925 | −1.159 | −3.269 | −1.803 | −6.234 |
| Bending bending | −0.154 | 0.841 | −0.003 | 3.044 | −0.426 | 8.513 |
| CONFLEX Energy most stable conformer | 74.127 | −48.229 | 78.386 | −76.241 | 39.006 | −275.044 |
| No. conformers stored | 1131 | 46 | 438 | 24 | 498 | 9 |
| MOPAC/PM5 (heat of formation) | −715.945 | | −623.942 | | −1033.201 | |
| MOPAC/PM5/COSMO (heat of formation in water) | −788.083 | | −698.534 | | −1136.015 | |

Optimal geometry for the radiopharmaceutical Lu-PSMA-617

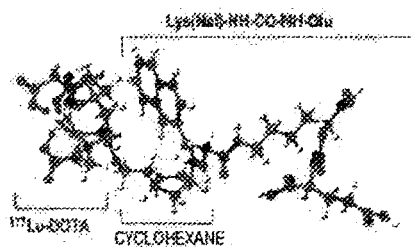

Optimal geometry for the radiopharmaceutical Lu-DOTA-HYNIC-IPSMA

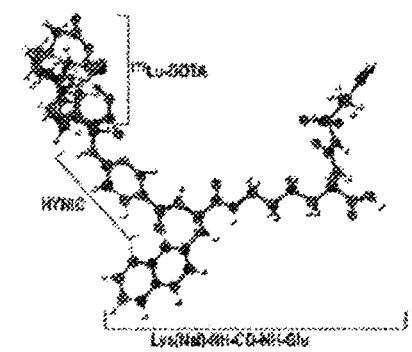

Optimal geometry for the radiopharmaceutical Lu-PSMA-I&T

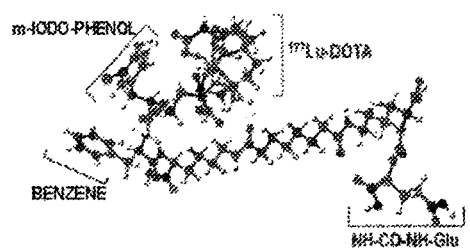

the lowest number of conformers with the lowest minimum energy, and the hydrophobic rings of the molecule are compromised in the conformation thereof when oriented, mainly due to said weak hydrogen interactions with the $^{177}$Lu-DOTA ring (benzene-[m-iodo-phenol]-$^{77}$Lu-DOTA interactions). As such, the optimal structural geometries of the different radiopharmaceuticals presented in table 1 indicate a suitable spatial conformation for Lu-DOTA-HYNIC-iPSMA, which results in a spatial orientation (with no significant intramolecular interactions) for the active site (Lys(NaI)-NH—CO—NH-Glu) of the molecule that favors biological recognition by the protein PSMA. In other words, the three carboxyl groups of the Glu-NH—CO—NH-Lys fragment remain free to interact electrostatically with the peptide side chains at the active site of PSMA, the urea oxygen to coordinate to zinc, and the aromatic structure in NaI to couple to the active hydrophobic site in the enzyme.

Moreover, in the structure of the radiopharmaceutical to be patented, HYNIC is not used as a molecule for chelation to the radiometal, whereas in other radiopharmaceuticals, HYNIC is used only as a binfunctional agent for labelling with $^{99m}$Tc [Decristoforo C et al., $^{99m}$Tc-EDDA/HYNIC-TOC: a new $^{99m}$Tc-labelled radiopharmaceutical for imaging somatostatin receptor-positive tumours; first clinical results and intra-patient comparison with $^{111}$In-labelled octreotide derivatives; 2000, J Nucl Med 27; 1318-25; Ferro-Flores G et al. Preparation and Evaluation of $^{99m}$TTC-EDDA/HYNIC-[Lys$^3$]-Bombesin for Imaging of GRP Receptor-Positive Tumours. Nucl Med Comm, 2006, 27:371-376; González-Vázquez A et al. Dosimetry and Biokinetics of $^{99m}$Tc-EDDA/HYNIC-Tyr$^3$-Octreotide Prepared from Lyophilized Kits. Appl Red Isot, 2006, 64: 792-79; Ortiz-Arzate Z et al. Kit preparation and biokinetics in women of $^{99m}$Tc-EDDA/HYNIC-E-[c(RGDfK)]$_2$ for breast cancer imaging. Nucl Med Common, 2014, 35:423-32; Medina-Garcia V el al. A Freeze-Dried Kit Formulation for the Preparation of Lys$^{27}$ ($^{99m}$Tc-EDDA/HYNIC)-Exendin(9-39)/$^{99m}$Tc-EDDA/HYNIC-Tyr$^3$-Octreotide to Detect Benign and Malignant Insulinomas. Nucl Med Biol, 2015, 42: 911-916].

Method for Preparing the Radiopharmaceutical of the Invention

Figure 2:
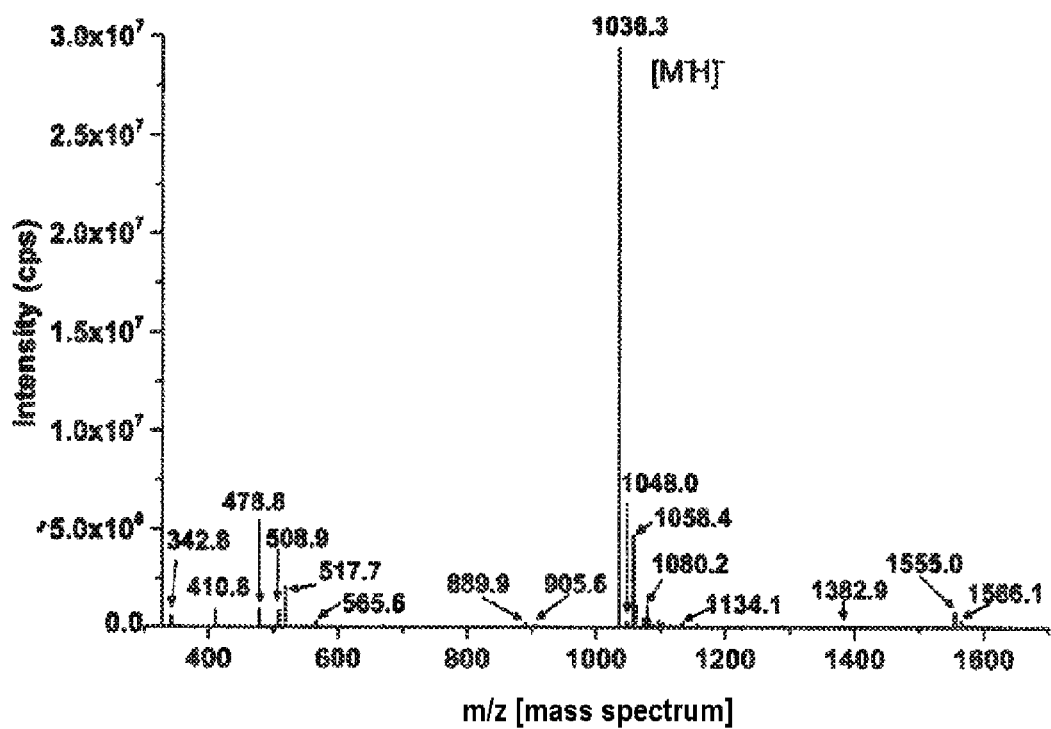
FIG. 2 shows the mass spectrum of Glu-NH—CO—NH-Lys(β-naphthyl alanine)-HYNIC-DOTA (DOTA-HYNIC-iPSMA).

The di-tert-butyl ester of glutamic acid was used initially to synthesise the molecule, said ester being reacted with carbonyldiimidazole (CDI) in the presence of triethylamine (TEA) to form the acylimizazole derivative, which was activated with methyl triflate (MeOTf) to react with (S)-tert-butyl-2-amino-6-(benzyloxycarbonylamino) hexanoate (Cbz-Lys-Ot-Bu), with subsequent deprotection of the Cbz by hydrogenolysis, thus giving the derivative Glu-Urea-Lys, which was reacted with the amino acid Fmoc-β-naphthyl alanine (HBTU/HOBt) in the solid phase (MBHA resin), followed by 6-Boc-hydrazinopyridin-3-carboxylic acid (Boc-HYNIC) in the presence of diisopropylethylenamine (DIPEA) and dimethylformamide (DMF) followed by addition of TFA. This latter addition step was repeated to introduce DOTA-tris (t-Bu ester) Finally, the compound was deprotected with TFA, purified by HPLC, and lyophilised. The final product was Glu-NH—CO—NH-Lys(β-naphthyl alanine)-HYNIC-DOTA (DOTA-HYNIC-iPSMA), which presented the expected mass spectrum shown in FIG. 2. Reverse-phase HPLC analysis of the lyophilised white solid showed a chemical purity of 98.8% for the compound.

Figure 3:
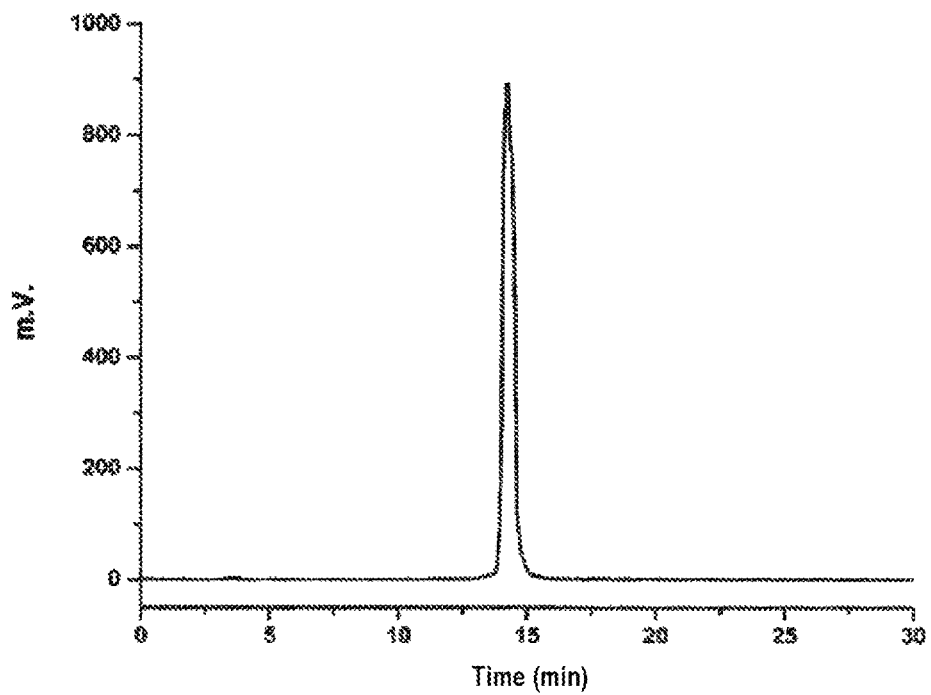
FIG. 3 shows the radio-chromatogram of 177Lu-DOTA-HYNIC-iPSMA.

DOTA-HYNIC-iPSMA (0.6 mg) was formulated as a lyophilised pharmaceutical form containing 50 mg mannitol and 100 mg ascorbic acid. After reconstitution in 1.1 mL sodium acetate 1 M buffer solution pH 5.0 containing the sterile and pyrogen-free solution of lutetium-177 chloride ($^{177}$LuCl$_3$) and incubation in a dry bath at 95° C. for 30 minutes, said formulation gave a clear, aqueous solution of the compound to be patented $^{177}$Lu-DOTA-HYNIC-iPSMA (FIG. 1) with a radiochemical purity of more than 98%, as determined by reverse-phase HPLC, which presents the radio-chromatogram shown in FIG. 3.

The radiopharmaceutical remains stable, with a radiochemical purity of more than 98% for more than 7 days post-labelling. In vitro stability tests in human serum show a serum protein binding of 6.5±1.8% and a high radiochemical stability (>98%). The affinity of $^{177}$Lu-DOTA-HYNIC-iPSMA, as determined from saturation studies in cancer cells positive for the protein PSMA (LNCaP), showed a $K_d$ of 6.33±2.69 nM and a maximum number of binding sites ($B_{max}$) of 5.89±0.47 nM.

The compound did not present toxicity or adverse effects when administered at a dose of 40 mg/kg in balb-C laboratory mice. Biodistribution assays for $^{177}$Lu-DOTA-HYNIC-iPSMA in nude mice with LNCaP-induced tumors showed an uptake in said tumors of 9.74±1.13% of the activity administered per gram of tissue (% ID/g) with a mainly renal elimination pathway.

To determine the biokinetics and dosimetry for the radiopharmaceutical, whole-body images were acquired for five healthy subjects at 20 mins and 6, 24, 48 and 120 h post-administration of $^{177}$Lu-DOTA-HYNIC-iPSMA (185 MBq). The sequence of images was used to extrapolate the time-activity curves in each organ to adjust the biokinetic model and calculate the total number of disintegrations (N) that occurred in the source regions. The values of N were used in the OLINDA/EXM code to calculate the internal doses of radiation. The images in healthy volunteers showed fast clearance, with a half life of 1.1 h for the fast component ($T_{1/2}\alpha$=ln 2/0.614), 9.2 h for the first slow component ($T_{1/2}\beta$=ln 2/0.075), and 79.6 h for the second slow component ($T_{1/2}\gamma$=ln 2/0.008). Uptake and excretion is mainly renal, with lower hepatic uptake and high uptake in the parathyroid, salivary, and lachrymal glands. The average doses absorbed were 0.23, 0.28, 0.88, and 1.17 mGy/MBq for the spleen, liver, kidney, and salivary glands, respectively.

To evaluate the radiotherapeutic potential, between one and four cycles of $^{177}$Lu-DOTA-HYNIC-iPSMA (3.7 or 7.4 GBq) were administered to 11 patients (mean age: 66 years; range: 45-86) every 8-10 weeks. The response was evaluated using images with $^{68}$Ga-PSMA-11 PET/CT (radiopharmaceutical with a proven affinity in clinical practice and a high-resolution technique for the specific detection of metastatic prostate cancer lesions) and determining serum prostate-specific antigen (PSA) levels before and after treatment. Around 60% of patients exhibited a reduction in PSA and 70% a reduction in the number and size of metastatic lesions and/or in the uptake intensity of the radiopharmaceutical in the metastases and the primary tumor, as determined by imaging.

Figure 4:
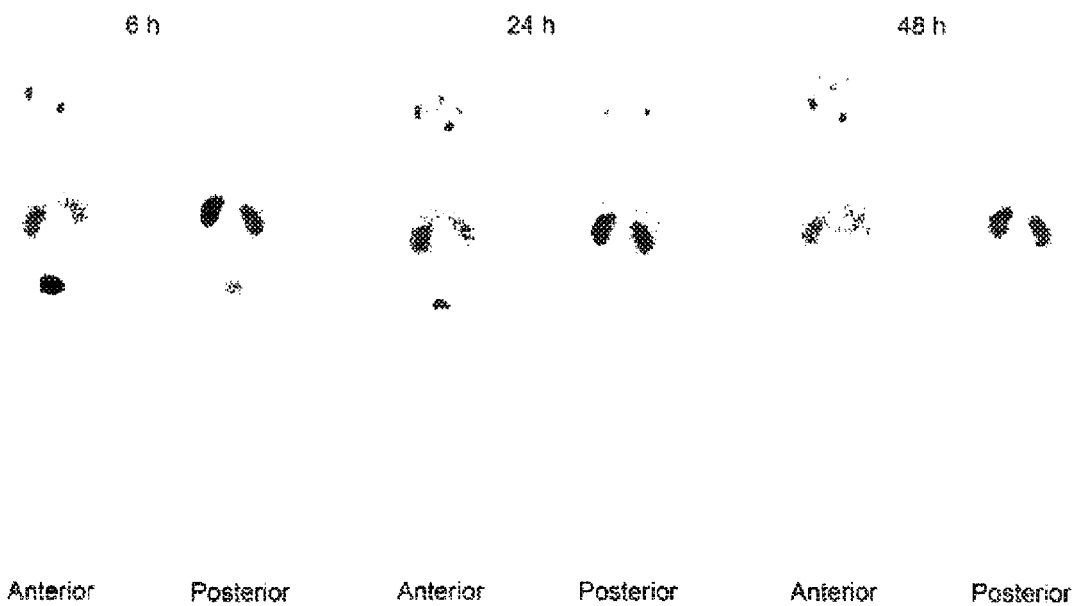
FIG. 4 shows a SPECT image for the radiopharmaceutical 177Lu-DOTA-HYNIC-iPSMA obtained in a healthy volunteer at different times.
Figure 5:
FIG. 5 shows PET and SPECT images of a patient with advanced metastatic prostate cancer who received both 68Ga-PSMA-11 (PET, 1 h) and 177Lu-DOTA-HYNIC-iPSMA (SPECT, 24 h), showing that both radiopharmaceuticals detect prostate cancer tumors and metastases associated with overexpression of PSMA, thereby confirming the ability of the radiopharmaceutical 177Lu-DOTA-HYNIC-iPSMA to detect PSMA overexpressed in prostate cancer cells in vivo.
Figure 5:
Figure 6:
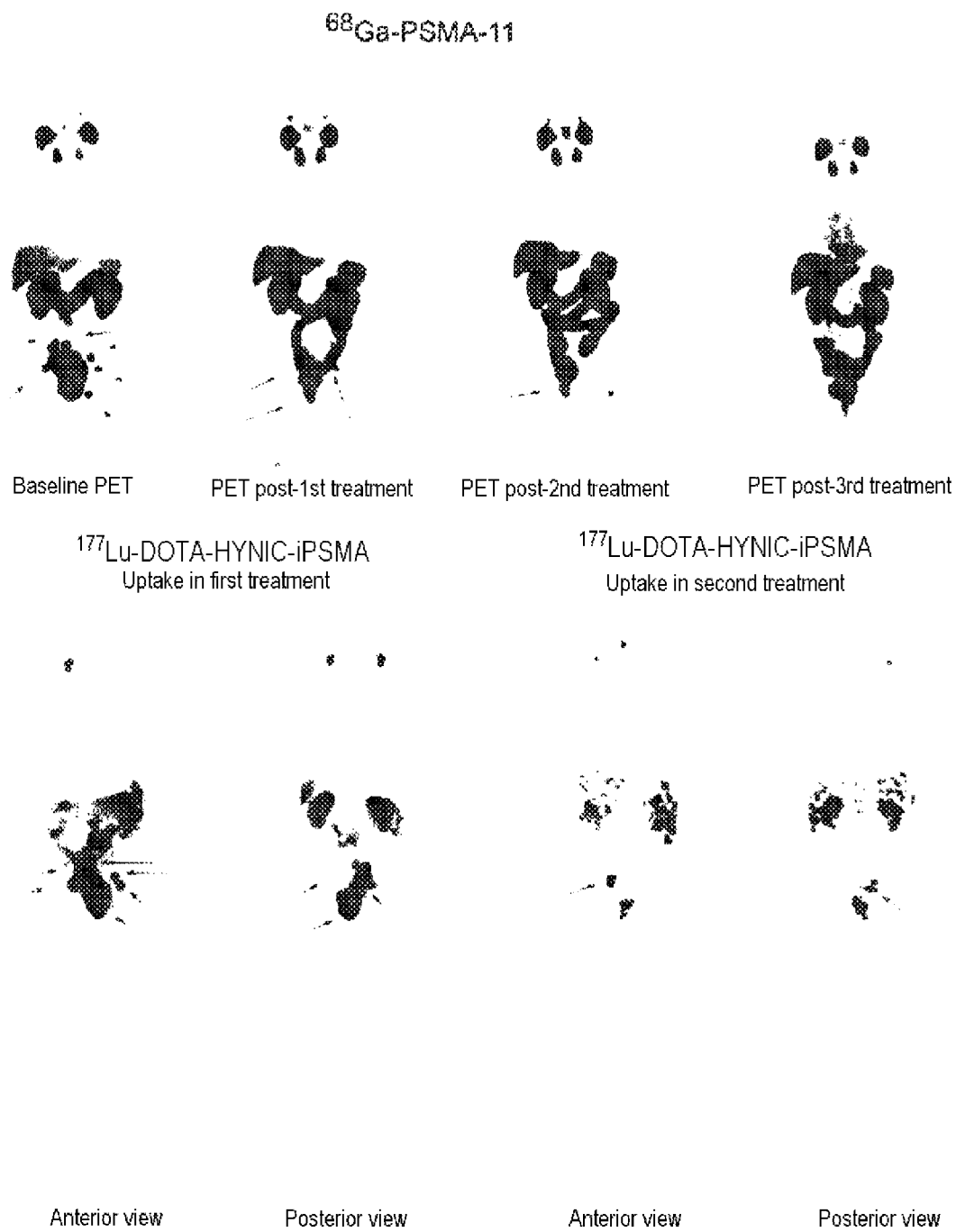
FIG. 6 shows images for a patient with metastatic prostate cancer after three cycles of treatment with 177Lu-DOTA-HYNIC-iPSMA. Imaging-based follow-up with 68Ga-PSMA-11 (PET) shows that the prostate cancer metastatic lesion sites (indicated with an arrow) decrease in size and number after each administration of 177Lu-DOTA-HYNIC-iPSMA until complete elimination.

FIG. 4 shows a SPECT image for the radiopharmaceutical $^{177}$Lu-DOTA-HYNIC-iPSMA obtained in a healthy volunteer at different times. FIG. 5 shows a PET and SPECT image of the same patient with advanced metastatic prostate cancer who received both $^{68}$Ga-PSMA-11 (PET, 1 h) and $^{177}$Lu-DOTA-HYNIC-iPSMA (SPECT, 24 h), showing that both radiopharmaceuticals detect prostate cancer tumors and metastases, associated with overexpression of PSMA, thereby confirming the ability of the radiopharmaceutical $^{177}$Lu-DOTA-HYNIC-iPSMA to detect the PSMA overexpressed in prostate cancer cells in vivo. Finally, FIG. 6 shows images for a patient with metastatic prostate cancer after the third cycle of treatment with $^{177}$Lu-DOTA-HYNIC-iPSMA. Imaging-based follow-up with $^{68}$Ga-PSMA-11 (PET) shows that the prostate cancer metastatic lesion sites (indicated with an arrow) decrease in size and number after each administration of $^{177}$Lu-DOTA-HYNIC-iPSMA until complete elimination. Said image confirms and is the main evidence for the radiotherapeutic potential of $^{177}$Lu-DOTA-HYNIC-iPSMA for the treatment of tumoral lesions overexpressing PSMA.

In conclusion, $^{177}$Lu-DOTA-HYNIC-iPSMA is obtained with the following features:

A radiochemical purity of greater than 98%.

The ability of the radiopharmaceutical to detect tumors overexpressing prostate-specific membrane antigen in vivo associated with a favorable spatial orientation of the active site (Lys(Nal)-NH—CO—NH-Glu) of the molecule induced by the presence of HYNIC bound to the DOTA molecule.

As a result of the molecular recognition associated with a favorable spatial orientation of the active site (Lys(Nal)-NH—CO—NH-Glu) of the molecule induced by the presence of HYNIC bound to the DOTA molecule and labeled with lutetium-177, the radiopharmaceutical $^{177}$Lu-DOTA-HYNIC-iPSMA exhibits radiotherapeutic properties, as shown by the significant reduction in serum PSA levels and a decrease in the number and size of metastatic lesions observed in prostate cancer patients treated with $^{177}$Lu-DOTA-HYNIC-iPSMA.

The invention claimed is:

1. A compound comprising a chelator-hydrazinonicotinamide (HYNIC)-prostate specific membrane antigen inhibitor (iPSMA), wherein the chelator is 1,4,7,10-tetraazacyclodo-decano-N,N',N'',N'''-tetraacetic acid (DOTA), and wherein the compound has the structure

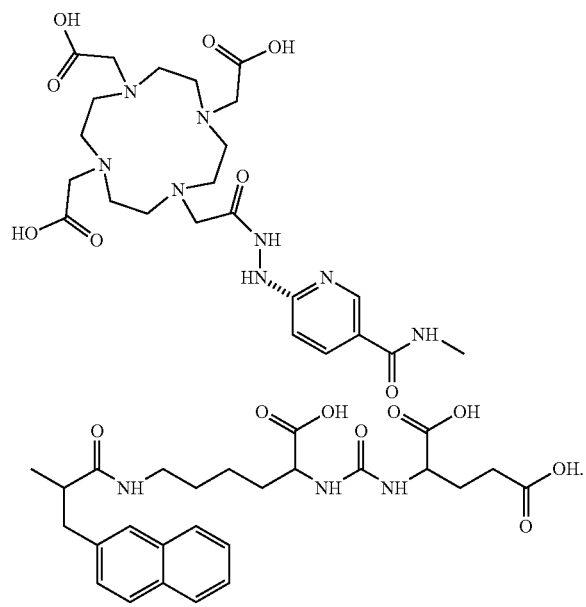

2. A radiopharmaceutical comprising the compound of claim 1 and a radionuclide.

3. The radiopharmaceutical of claim 2 having the formula $^{177}$Lu-DOTA-HYNIC-iPSMA and comprising the structure

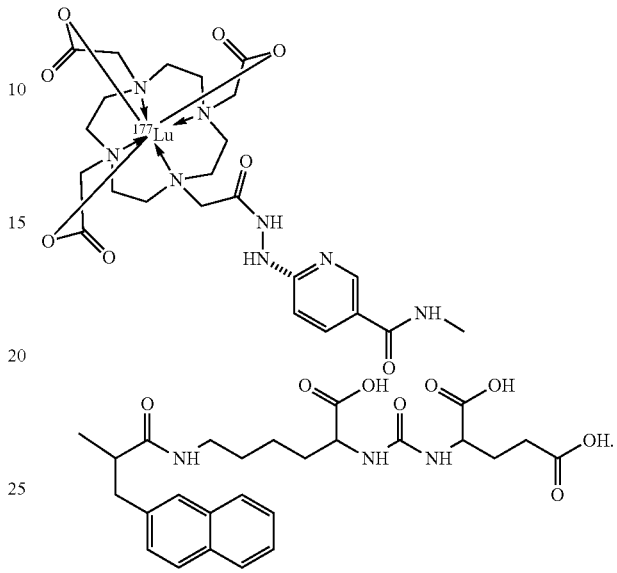

4. A radiopharmaceutical composition comprising the radiopharmaceutical of claim 3.

5. The radiopharmaceutical composition of claim 4 comprising a 1 M sodium acetate buffer solution, pH 5.0.

6. The compound of claim 1 (DOTA-HYNIC-iPSMA) formulated as a lyophilized pharmaceutical form, for use in radiolabeling.

7. The compound of claim 6, wherein the lyophilized pharmaceutical form contains 50 mg mannitol and 100 mg ascorbic acid.

8. A kit comprising
the compound of claim 1 (DOTA-HYNIC-iPSMA) formulated as a lyophilized pharmaceutical form containing 50 mg mannitol and 100 mg ascorbic acid, and
a 1 M sodium acetate buffer solution, pH 5.0, containing a radionuclide,
for use in radiolabeling.

9. A method of treating a patient with a tumor expressing prostate-specific membrane antigen (PSMA) protein, the method comprising administering to the patient a therapeutically effective amount of the radiopharmaceutical of claim 3.

10. The method of claim 9, wherein administration of the radiopharmaceutical to the patient is effective to decrease size and/or number of prostate cancer metastatic lesion sites.

* * * * *